United States Patent
Gross

(10) Patent No.: US 12,350,091 B2
(45) Date of Patent: Jul. 8, 2025

(54) RETRACTABLE STETHOSCOPE

(71) Applicant: Mark Gross, Denver, CO (US)

(72) Inventor: Mark Gross, Denver, CO (US)

( * ) Notice: Subject to any disclaimer, the term of this patent is extended or adjusted under 35 U.S.C. 154(b) by 1657 days.

(21) Appl. No.: 16/198,714

(22) Filed: Nov. 21, 2018

(65) Prior Publication Data

US 2020/0155112 A1    May 21, 2020

(51) Int. Cl.
  *A61B 7/02* (2006.01)
  *A61B 50/30* (2016.01)
  *A61B 50/31* (2016.01)
  *A61B 90/53* (2016.01)

(52) U.S. Cl.
  CPC .............. *A61B 7/02* (2013.01); *A61B 50/31* (2016.02); *A61B 90/53* (2016.02); *A61B 2050/301* (2016.02); *A61B 2050/311* (2016.02)

(58) Field of Classification Search
  CPC ........... A61B 7/02; A61B 50/31; A61B 90/53; A61B 2050/301; A61B 2050/311; A61B 7/023; A61B 7/026; A61B 7/04; A61B 7/045; H04R 1/1033; H02G 11/02; B65H 75/4431
  USPC ............................. 181/131; D24/134; 73/591
  See application file for complete search history.

(56) References Cited

U.S. PATENT DOCUMENTS

| | | | |
|---|---|---|---|
| 742,790 A | * | 10/1903 | Jones |
| 3,621,845 A | * | 11/1971 | Oates ................. A61B 5/02233 |
| | | | D24/134 |
| 3,798,389 A | | 3/1974 | Tokizaki |
| 5,422,957 A | | 6/1995 | Cummins |
| 6,480,611 B2 | | 11/2002 | Hashimoto |
| 6,616,080 B1 | | 9/2003 | Edwards |
| 7,201,342 B2 | * | 4/2007 | Huang ................ B65H 75/4431 |
| | | | 242/378.2 |
| 7,346,174 B1 | * | 3/2008 | Smith .................... G16H 40/63 |
| | | | 600/528 |
| 7,357,666 B2 | | 4/2008 | Wu |
| 7,372,974 B2 | | 5/2008 | Yanagishita |

(Continued)

FOREIGN PATENT DOCUMENTS

| | | | |
|---|---|---|---|
| CN | 205286395 U | * | 6/2016 |
| CN | 205322354 U | * | 6/2016 |

(Continued)

OTHER PUBLICATIONS

Machine Translation of CN 106955123 A. Inventor—Yu. Title—"A Telescopic Multifunctional Stethoscope For Medical". Published—Jul. 18, 2017 (Year: 2017).*

(Continued)

*Primary Examiner* — Dedei K Hammond
*Assistant Examiner* — Jennifer B. Olson
(74) *Attorney, Agent, or Firm* — The Lisa Foundation Patent Law Clinic; Anthony Bonfiglio

(57) ABSTRACT

A retractable stethoscope comprising a case, at least one piece of acoustic tubing, at least one ear piece, and a chest piece. The chest piece is coupled to one end of the acoustic tubing, and at least one ear piece is coupled to another end of the acoustic tubing. The length of the acoustic tubing may extend from and retract into the case from the ear piece end, the chest piece end of the acoustic tubing, or both ends either independently or simultaneously. The retractable stethoscope may further comprise a belt clip.

17 Claims, 14 Drawing Sheets

(56) References Cited

U.S. PATENT DOCUMENTS 7,636,445 B2 * 12/2009 Yoshimine ............... A61B 7/04
381/67
D673,269 S * 12/2012 El-Mohtar .................. D24/134

FOREIGN PATENT DOCUMENTS

| CN | 206166935 U | * | 5/2017 | |
|---|---|---|---|---|
| CN | 206381187 U | * | 8/2017 | |
| CN | 207055505 U | * | 3/2018 | |
| JP | H03168125 A | * | 7/1991 | |
| WO | WO-2011120965 A1 | * | 10/2011 | ......... B65H 75/4431 |

OTHER PUBLICATIONS

Machine Translation of CN 204950988 U. Inventor—Wang et al. Title—"A Heart Stethoscope For Internal Medicine". Published—Jan. 13, 2016 (Year: 2016).*
Machine Translation of JP H03168125 A. Inventor—岸上 正義 (Kishigami Masayoshi ). Title—"Reel Type Stethoscope". Published—Jul. 19, 1991 (Year: 1991).*
Machine translation of CN-206080555-U. Inventor: Guo (Year: 2017).*
"ECHO Retractable Stethoscope." Youtube, uploaded by Mark Gross, Aug. 20, 2018, https://www.youtube.com/watch?v=ph9uOfsxrBE (Year: 2018).*
Machine translation of CN-205286395-U (Year: 2016).*
Machine translation of CN-205322354-U (Year: 2016).*
Machine translation of CN-206381187-U (Year: 2017).*
Machine translation of CN-206166935-U (Year: 2017).*
Machine translation of CN-207055505-U (Year: 2018).*

* cited by examiner

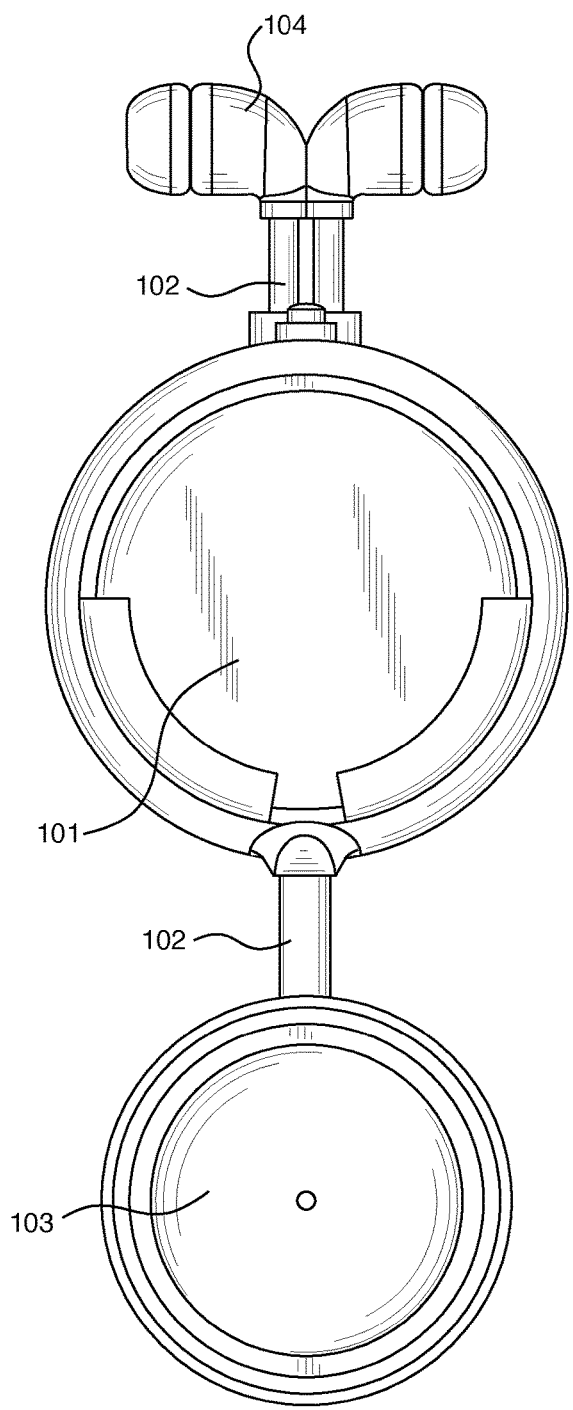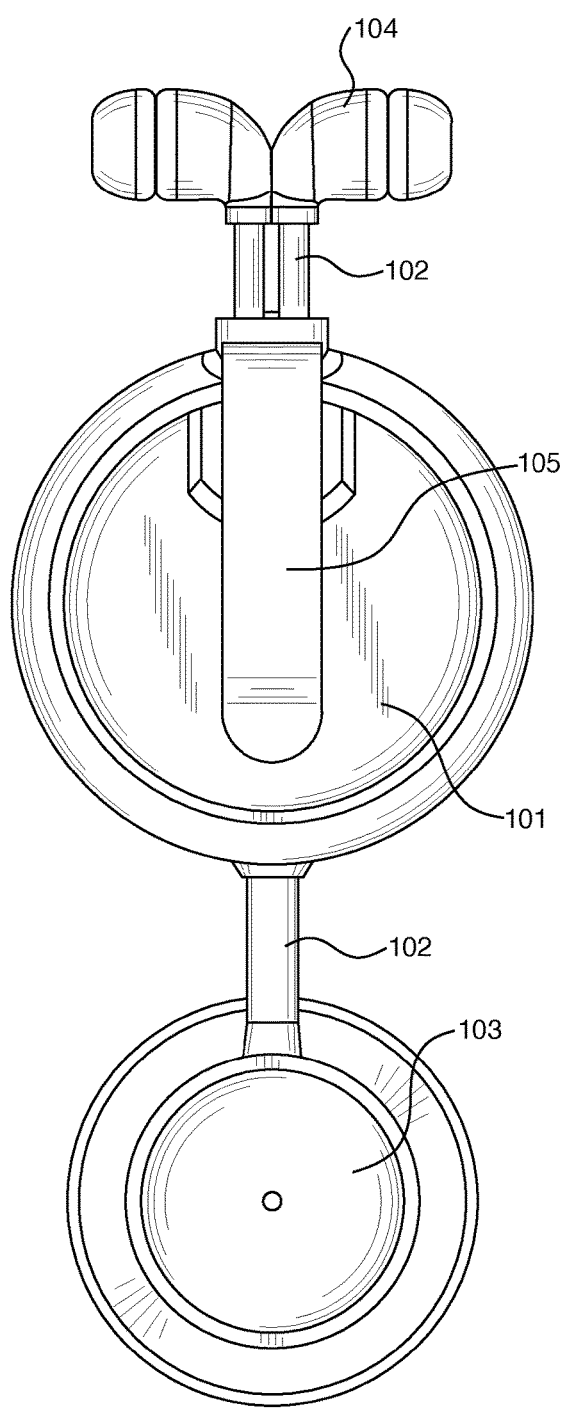
FIG. 3
FIG. 4

RETRACTABLE STETHOSCOPE

CROSS-REFERENCE TO RELATED APPLICATIONS

This application claims priority to U.S. Provisional Application No. 62/589,395, which is incorporated by reference herein in its entirety.

FIELD OF THE INVENTIONS

The inventions described herein generally pertain to stethoscopes used for diagnostic auscultation. More particularly, the inventions described herein pertain to a retractable stethoscope providing for adjustment of the distance between the stethoscope ear piece(s) and the stethoscope chest piece.

INTRODUCTION

Most stethoscopes comprise fixed-length tubing for the transmission of acoustic signals from stethoscope chest piece to at least one ear piece. This design may limit the usability of the stethoscope and be inconvenient for the user. Additionally, this standard design may lead to accidental contamination of the stethoscope due to its traditionally unwieldy anatomy.

Retractable winding mechanisms for cabling or tubing are common among audio recording and playback devices. Such devices commonly comprise cabling for the transmission of electrical signals from an audio playback device to at least one ear piece and a winding mechanism within a housing for extending, retracting, and storing the length of the cabling.

To reduce the complexity and length of this specification, the materials identified in the following paragraphs of this section are herein expressly incorporated by reference in their entirety. The incorporated material is believed to be non-essential in accordance with 37 CFR 1.57 because it is referred to for purposes of providing general support, background, or information relating to the inventions. However, if any such material is deemed essential under Rule 1.57, any such text will be expressly added herein pursuant to the applicable rules.

U.S. Pat. No. 3,798,389 of Tokizaki describes a headphone comprising a case having an annular recess in which a freely rotatable reel for the internal storage of a cord is mounted.

U.S. Pat. No. 5,422,957 of Cummins describes a cable take-up for earphones comprising a cylindrical case having a cable wound onto a rotating spool biased by a spring to retract the cable, a ratchet to prevent the cable from retracting, and an externally accessible release for the ratchet.

U.S. Pat. No. 6,616,080 of Edwards describes a retractable cord device comprising an automatic retraction and storage method for a cable or cord wherein one end of the cord may be fixed and the other extracted and retracted, or both ends may be extracted and retracted simultaneously.

U.S. Pat. No. 7,357,666 of Wu describes a cable winder using the spring force of a spiral spring to pull back a signal transmission cable automatically and a clamping part and a spiral rail for retaining the cable by sections.

U.S. Pat. No. 6,480,611 or Hashimoto describes a headphone having a cord reel comprising a winding mechanism in a housing assembly for winding an input cord into the housing assembly, including a cord reel biased to wind the input cord therearound.

U.S. Pat. No. 7,372,974 of Yanagishita describes a headphone with cord winder devices for winding up an input cord and a bridging cord.

BRIEF SUMMARY OF THE INVENTION

Unless specifically noted, words and phrases in this specification and the claims are to be given their plain and ordinary English meaning. Thus, except where this specification uses the exact phrase "[word or phrase] is hereby defined to mean [definition]," the inventor expressly elects, as his own lexicographer, to use the plain and ordinary meaning of words in the specification and claims rather than a special definition. Absent such specific statement to apply a special definition, the plain and ordinary meaning applies to the terms used in the specification and claims.

The inventor is also aware of the normal precepts of English grammar. Thus, if a noun, term, or phrase is intended to be characterized, specified, limited, broadened, modified or narrowed in some way, the such noun, term, or phrase will expressly include any desired or intended adjectives, descriptive terms, or other modifiers in accordance with the normal precepts of English grammar. Absent the use of such adjectives, descriptive terms, or modifiers in the claim language, it is intended that such nouns, terms, or phrases be given their plain and ordinary English meaning in the field.

Further, the inventor is aware of the availability and limits of functional claiming under 35 U.S.C. § 112(f). As used herein or in the claims, the words "function," "means" or "step" do not indicate an intent to invoke the special provisions 35 U.S.C. § 112(f) to define the inventions. To the contrary, if the provisions of 35 U.S.C. § 112(f) are sought to be invoked to define the inventions, the claims will specifically and expressly recite the exact phrase "means for" and will also expressly recite the word "function" followed by a description of the function (i.e., will state: "means for performing the function of [insert function]"), without also reciting in such phrases any structure, material or act in support of the function. Thus, even if a claim recites a "means for performing the function of . . . " if a claim also recites any supporting structure, material or acts then it is the clear intention of the inventor not to invoke the provisions of 35 U.S.C. § 112(f). If the provisions of 35 U.S.C. § 112(f) are invoked to define the claimed inventions (using the technique defined above), it is intended that the inventions not be limited only to the specific structure, material or acts that are described in any specific embodiment, but in addition, include any equivalent structures, materials, or acts that perform the claimed function, or any structures, materials, or acts described in any alternative situations or forms of the inventions, or that are within the appropriate limits of claim scope and construction and that are reasonably described and reasonably enabled by this specification.

The inventions described in this specification and recited in the claims are not directed to laws of nature, natural phenomena, or abstract ideas, but instead, are directed to one or more of the expressly permitted statutory categories of inventions, i.e., processes, machines, manufactures, or compositions of matter. Nor are the inventions claimed herein directed to any prohibited examples of abstract ideas such as fundamental economic practices, methods of organizing human activity, an idea itself, or any mathematical relationships/formulas. To be clear, the claimed inventions are directed to significantly more than any abstract idea by itself.

Numerous possible or potential aspects, objects, modifications, features, uses, or advantages of various inventions described herein will be apparent to those of ordinary skill in the art from this specification, drawings, and claims. However, without characterizing or limiting the scope of the various inventions as they are claimed, some of the possible or potential aspects, objects, features, uses, or advantages of various inventions are summarized below. None of the following possible or potential aspects, objects, features, uses, or advantages are a disavowal, disclaimer, characterization, or interpretation of any aspects of any of the claims. These possible or potential aspects, objects, features, uses, or advantages might apply to any or none of the claimed inventions.

Traditional stethoscopes are long and unwieldy, often hanging in an unrestrained manner from around the user's neck. This design—which allows the loose stethoscope to swing around the medical environment—can result in unintentional contamination of the device. It may be an object, goal, or advantage of some of the inventions to provide a tool for diagnostic auscultation that is compact, self-containing, and easy to store or access between uses, in turn decreasing the risk of accidental contamination of a stethoscope. These and other objects, goals, or advantages may be achieved by a retractable stethoscope.

A retractable stethoscope may comprise a case; at least one length of acoustic tubing having at least one continuous airpath within the tubing; a chest piece that may couple to one end of the acoustic tubing; and at least one ear piece that may couple to another end of the acoustic tubing. Each ear piece 104 may be in fluid communication with the chest piece 103 via the at least one continuous airpath within the acoustic tubing 102. The length of the acoustic tubing may be housed within the case.

A retractable stethoscope may be configured to extend from or retract into the case from either the ear piece end or the chest piece end of the acoustic tubing. A retractable stethoscope may also be configured to extend from and retract into the case from both the ear piece end and the chest piece end of the acoustic tubing, either independently or simultaneously.

A retractable stethoscope may be configured to constantly apply a retracting force to the acoustic tubing, or it may be configured to allow the acoustic tubing to be locked in one or more extended positions. Such design features may include—but are not limited to—reels having at least one locking tooth which may lock the retractable stethoscope in various extended positions corresponding to the size of the teeth; extension locks which may engage and disengage a locking function at the user's will, or impediments on the acoustic tubing itself that halt retraction, such as the ear piece, the chest piece, or a stopper. The locking function allows for the acoustic tubing to be kept in one or more unspooled positions having a distance between the chest piece and the ear piece that is increased over that of the stethoscope in its fully retracted position.

Additionally, the retractable stethoscope may feature a belt clip attached to the back of the retracting housing. A belt clip may allow for the retractable stethoscope to be conveniently stored and accessed by the user as needed by easily and securely clipping onto an article of the user's clothing, such as a belt, shirt, or lanyard. Alternatively, the retractable stethoscope case may be made of a magnetic material such that a user may quickly access or store the stethoscope on a compatible magnetic surface.

BRIEF DESCRIPTION OF THE DRAWINGS

A more complete understanding of the present invention may be derived by referring to the DETAILED DESCRIPTION when considered in connection with the figures. In the figures, like reference numbers refer to like elements or acts. While the figures provide several examples of aspects, elements, modifications, or components that may or may not be variously involved with the systems, methods, and devices described herein, the figures are not provided to define, limit, or affect the scope of the inventions claimed or described herein.

FIGS. 1 through 5 are views of a retractable stethoscope in a retracted position showing the acoustic tubing housed within the case and coupled to a chest piece on an end, and at least one ear piece on another end.

Figure 1:
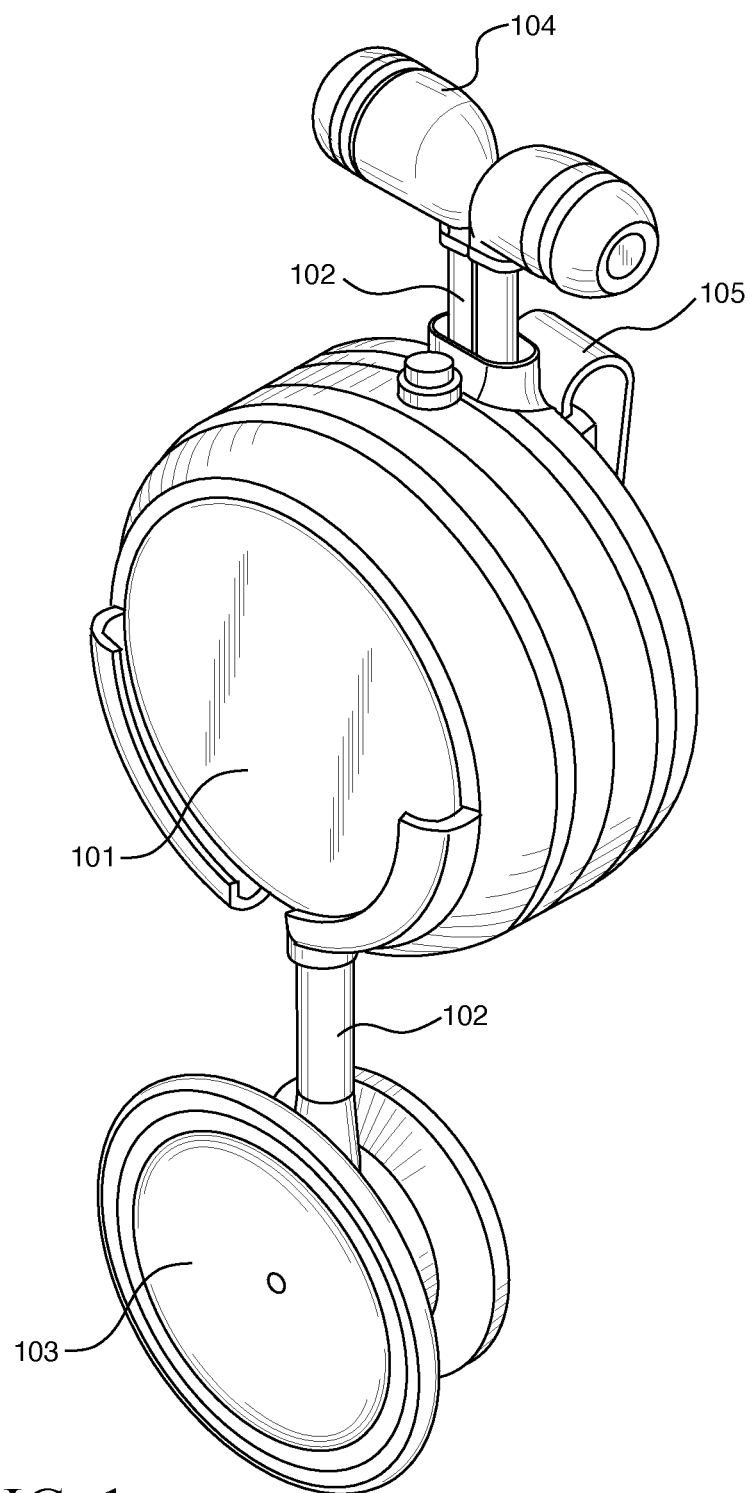
Figure 2:
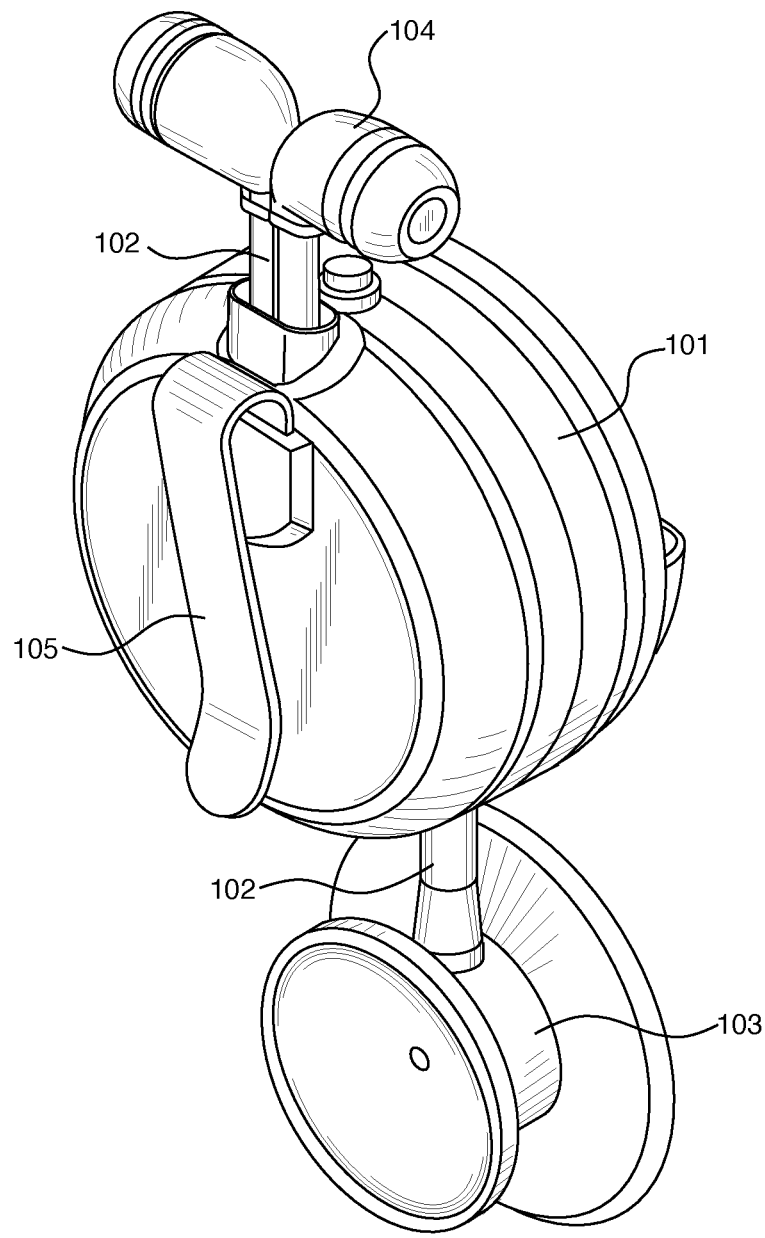
Figure 5:
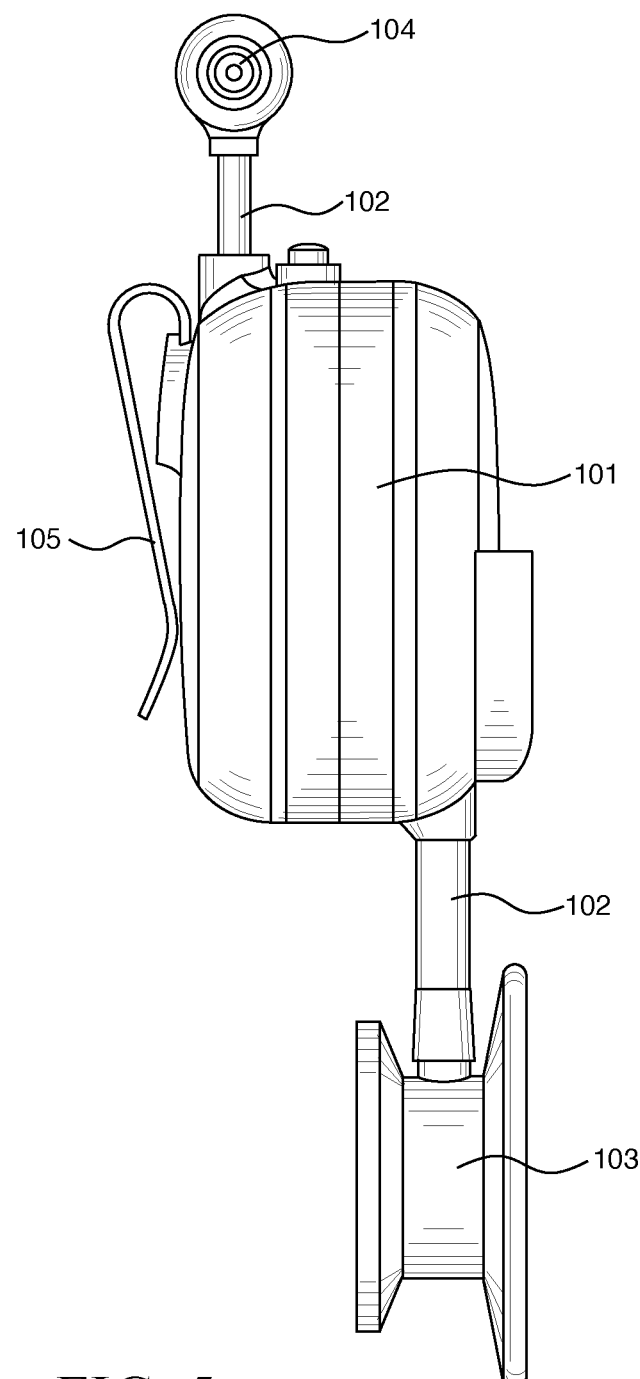
Figure 6:
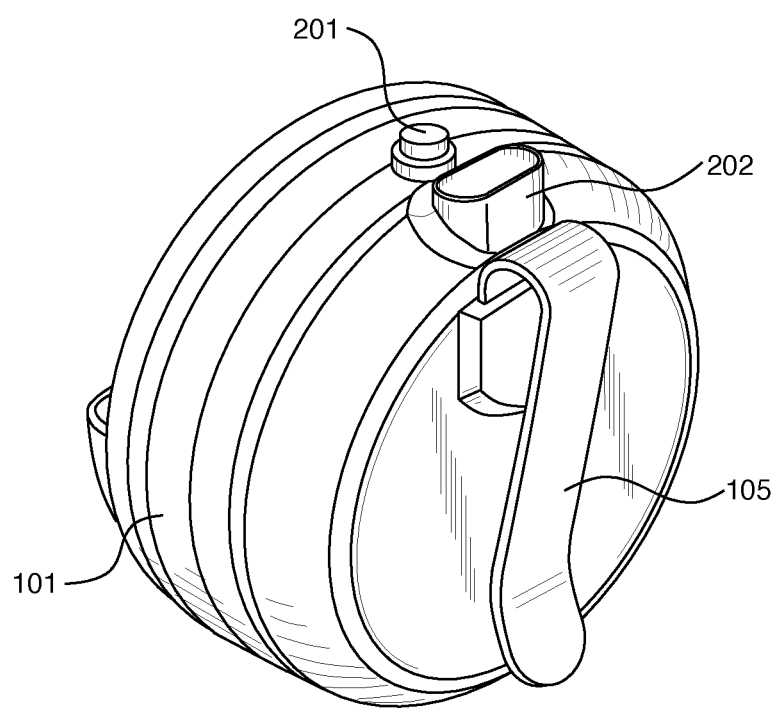
FIGS. 6 through 12 are views of a retractable stethoscope case showing the top and bottom tubing exits, an extension lock, and a belt clip coupled to the case.
Figure 7:
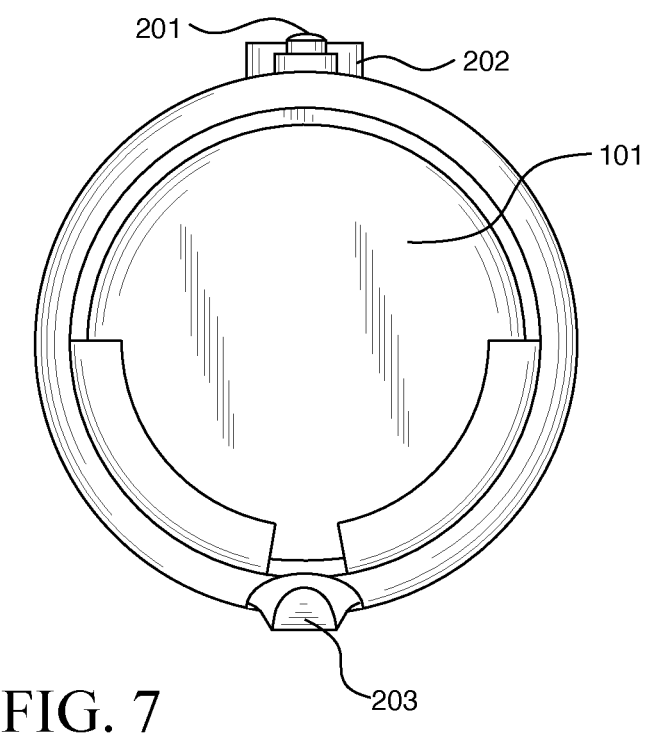
Figure 8:
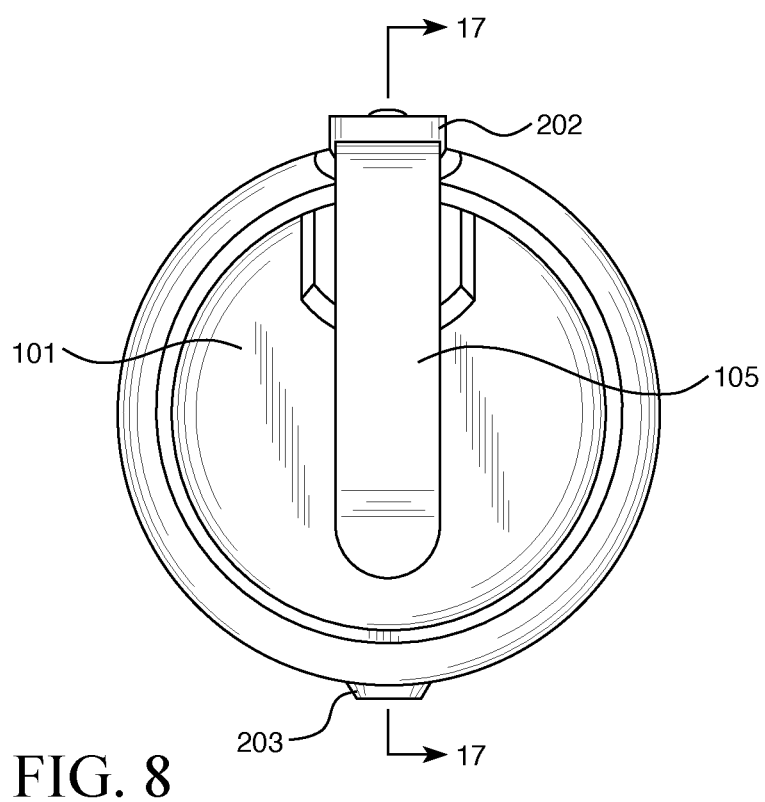
Figure 9:
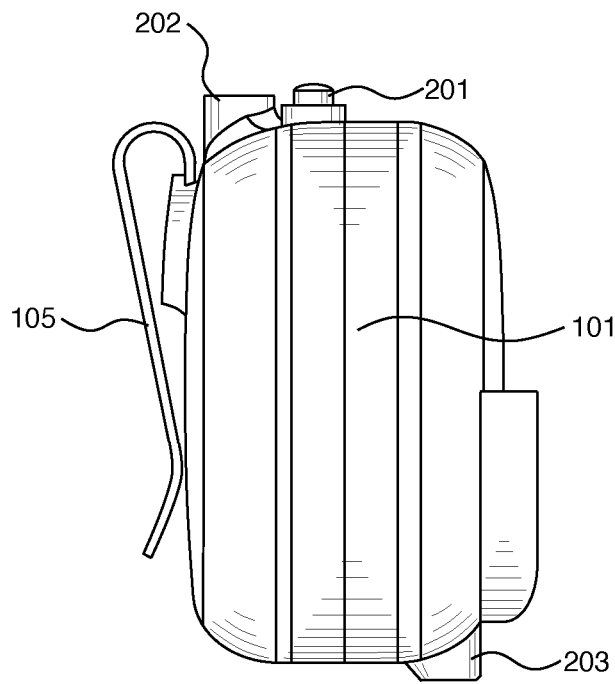
Figure 10:
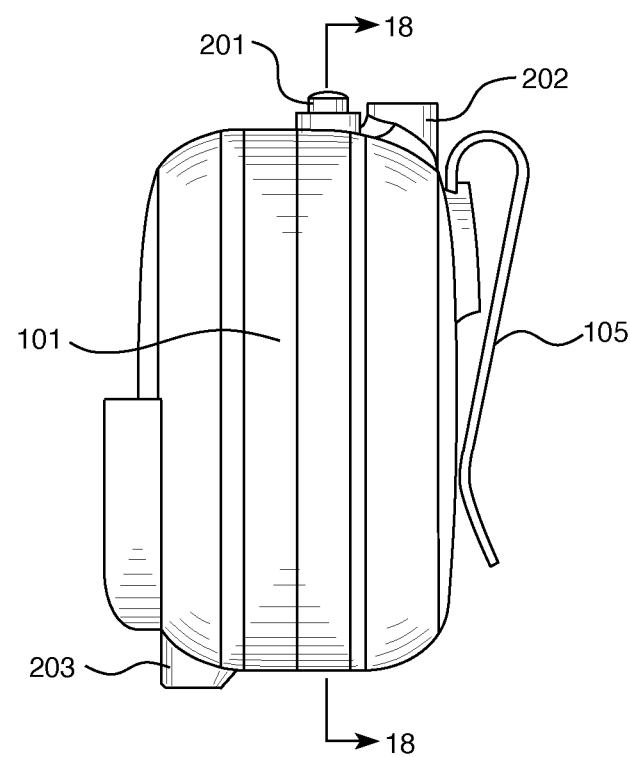
Figure 11:
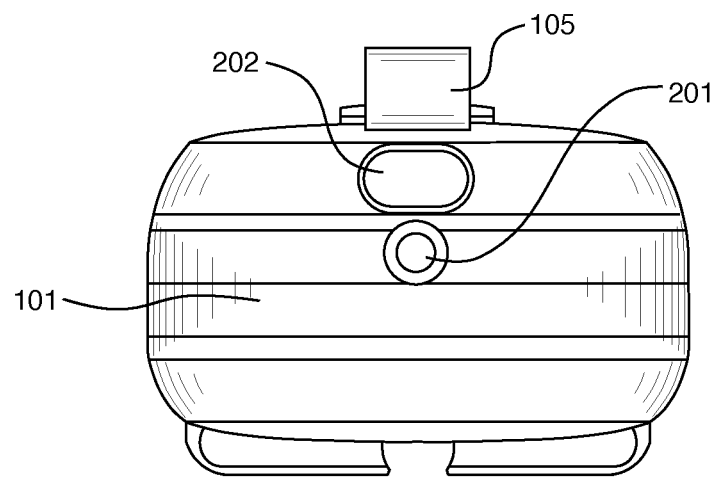
Figure 12:
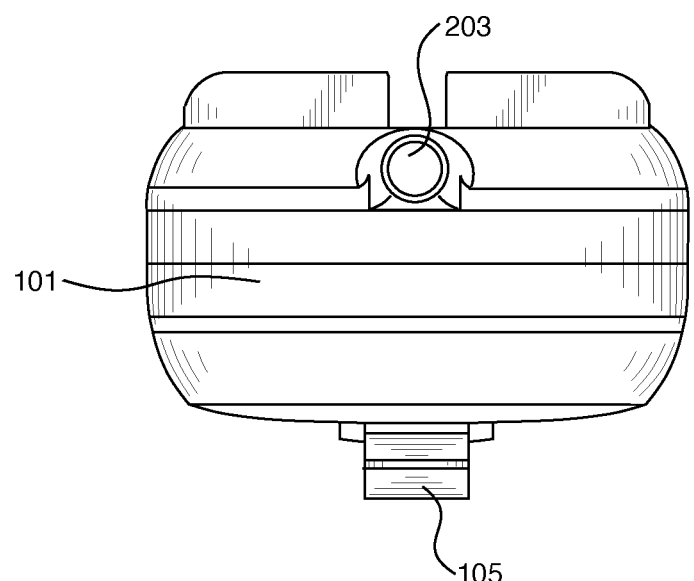

Elements and acts in the figures are illustrated for simplicity and have not been rendered according to any particular embodiment or example and are not to depict any essential or required limitations.

DETAILED DESCRIPTION

In the following description, and for the purposes of explanation, numerous specific details are set forth in order to provide a thorough understanding of the various aspects of the invention. However, it will be understood by those skilled in the relevant arts that the present invention may be practiced without these specific details. In other instances, known structures and devices are discussed more generally in order to avoid obscuring the invention. In many cases, a description of the operation is sufficient to enable one to implement the various forms of the invention. It should be noted that there are many different and alternative configurations, devices, and technologies to which the disclosed inventions may be applied. The full scope of the inventions is not limited to the examples that are described below.

FIGS. 1 through 5 show a retractable stethoscope. A retractable stethoscope may comprise a case 101, at least one length of acoustic tubing 102 having at least one continuous airpath, a chest piece 103, and at least one ear piece 104. The chest piece 103 may be used during diagnostic auscultation to pick up sounds within the body to be transferred through the acoustic tubing 102 to be heard by the user through the ear pieces 104. The chest piece 103 may be used by pressing it up against a patient's body. An ear piece 104 may be used by inserting the ear piece into the user's ear. Each ear piece 104 may be in fluid communication with the chest piece 103 via the at least one continuous airpath within the acoustic tubing 102. The length of the acoustic tubing 102 may be housed within the case 101. A retractable stethoscope may further comprise a belt clip 105 coupled to the case 101. The belt clip 105 may be used to conveniently store and access the retractable stethoscope by clipping onto an article of the user's clothing, such as a belt, a shirt, or a lanyard.

The case 101, shown in FIGS. 6 through 12, may feature an extension lock 201 that can be used to engage or disengage a locking function at the user's will. An extension lock 201 can be engaged to provide the acoustic tubing 102 with relief from the retracting pull force, allowing the acoustic tubing 102 to remain in an extended position. Once the extension lock 201 is disengaged, the retracting pull force will resume and the acoustic tubing 102 will be retracted from the extended position back into the case 101. The case 101 further comprises a top tubing exit 202 and a bottom tubing exit 203 through which the acoustic tubing 102 passes during extension and/or retraction.

Figure 13:
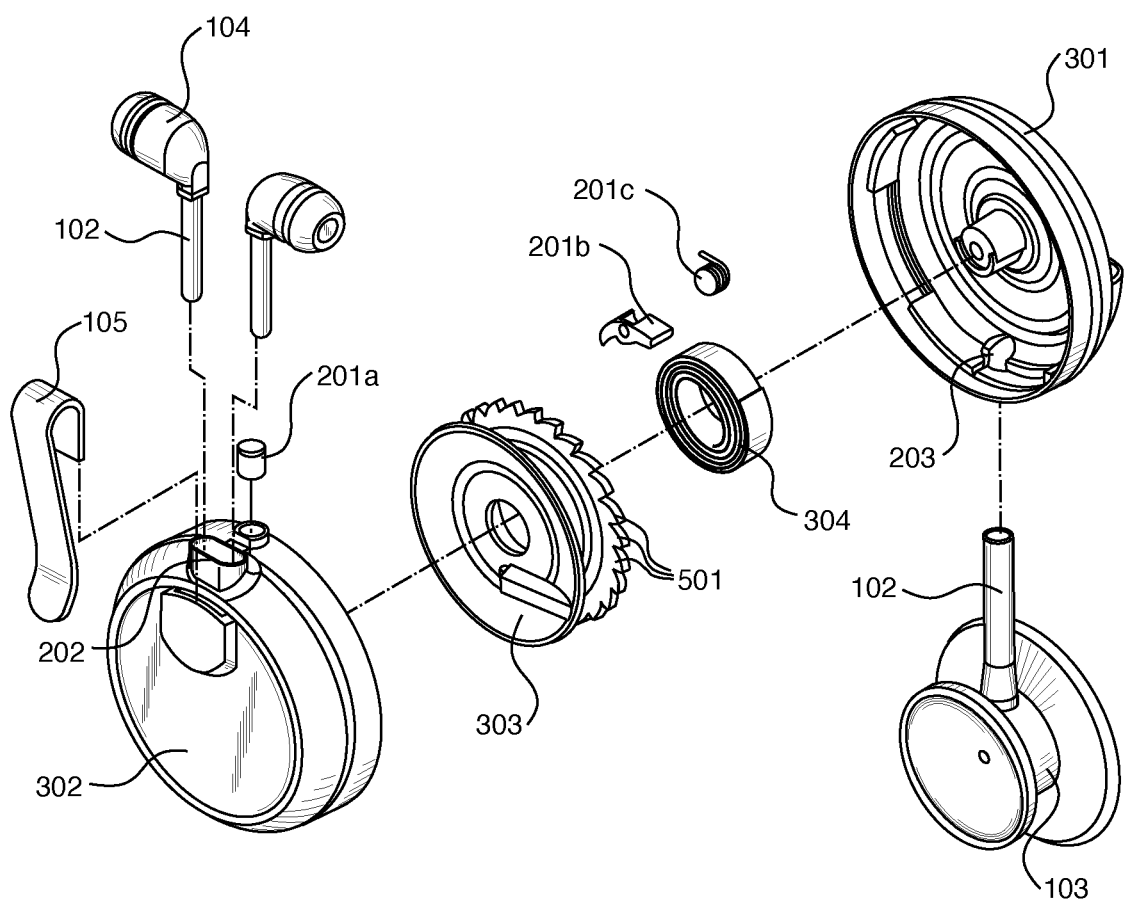
FIG. 13 is an exploded view of a one-way retractable stethoscope showing a single retracting reel around which the acoustic tubing may spool within the case.

FIG. 13 shows an exploded view of a one-way retractable stethoscope. A one-way retractable stethoscope may be configured to extended and retract either the ear piece 104 end or the chest piece 103 end of the acoustic tubing 102. A one-way retractable stethoscope case 101 may comprise a front case member 301 and back case member 302. Within the case 101, the retractable stethoscope may further comprise a retracting reel 303 and a reel tension spring 304. The retracting reel 303 may feature one or more locking teeth 501. The acoustic tubing 102 may be spooled around the retracting reel 303 having one end pass through the top tubing exit 202 and another end pass through the bottom tubing exit 203. The retractable stethoscope may be locked in various extended positions corresponding to the size and number of locking teeth 501 on the retracting reel 303. The retractable stethoscope may also be configured such that the reel tension spring 304 may apply a constant rotational force on the retracting reel 303. The constant rotational force results in a retracting pull force that is constantly applied to the acoustic tubing 102 by the retracting reel 303. In a constantly retracting configuration, a case 101 may further comprise an extension lock 201 that may comprise a lock top piece 201a coupled by a switch tension spring 201b to a locking switch 201c. The extension lock 201 may relieve and reapply the retracting pull force to the acoustic tubing 102 at the user's will. When engaging or disengaging the extension lock, the user can use the lock top piece 201a which remains accessible when the case is fully assembled.

Figure 14:
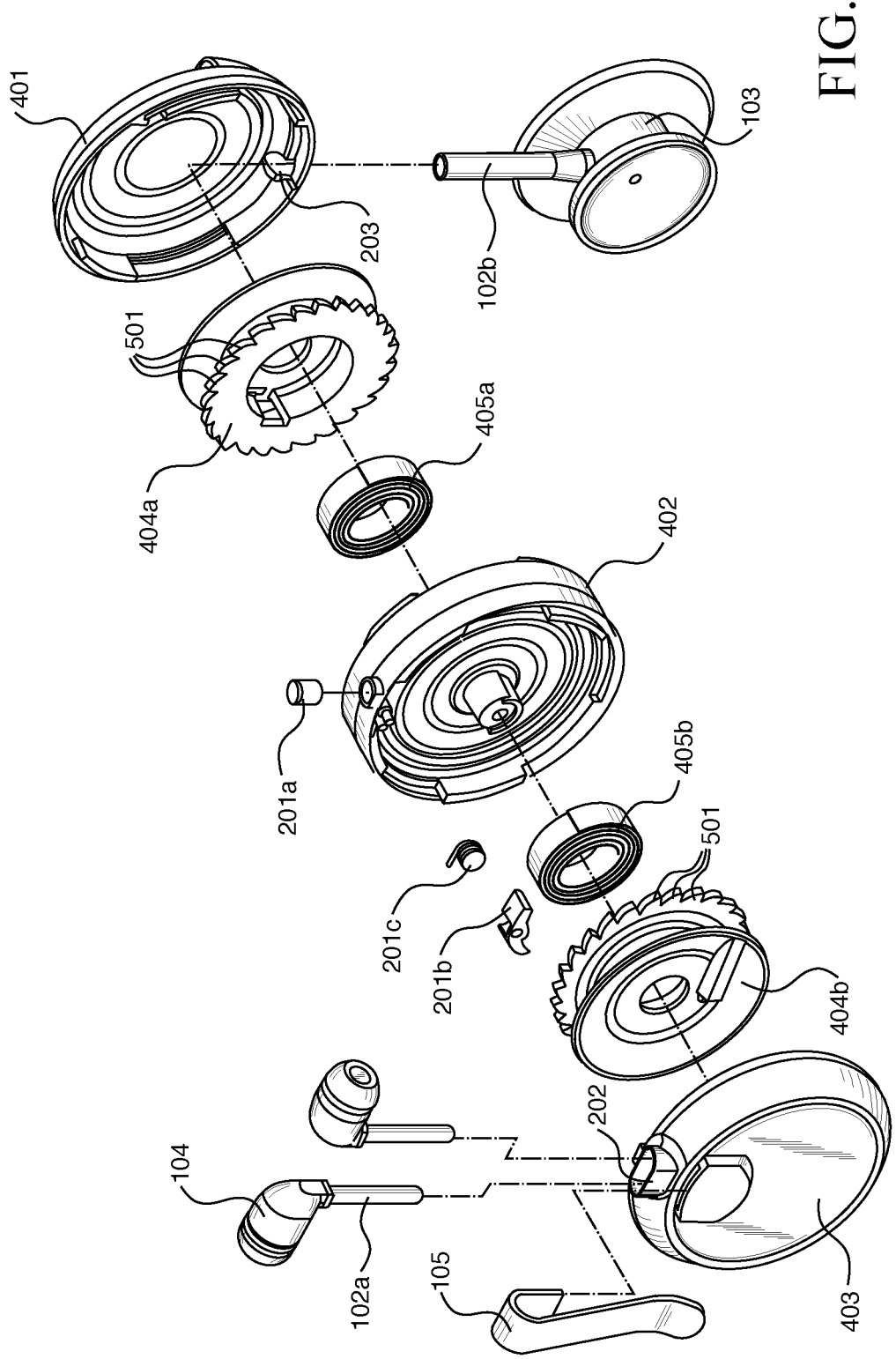
FIG. 14 is an exploded view of a first embodiment of two-way retractable stethoscope showing two retracting reels around which the top and bottom pieces of acoustic tubing may spool within the case.
Figure 15:
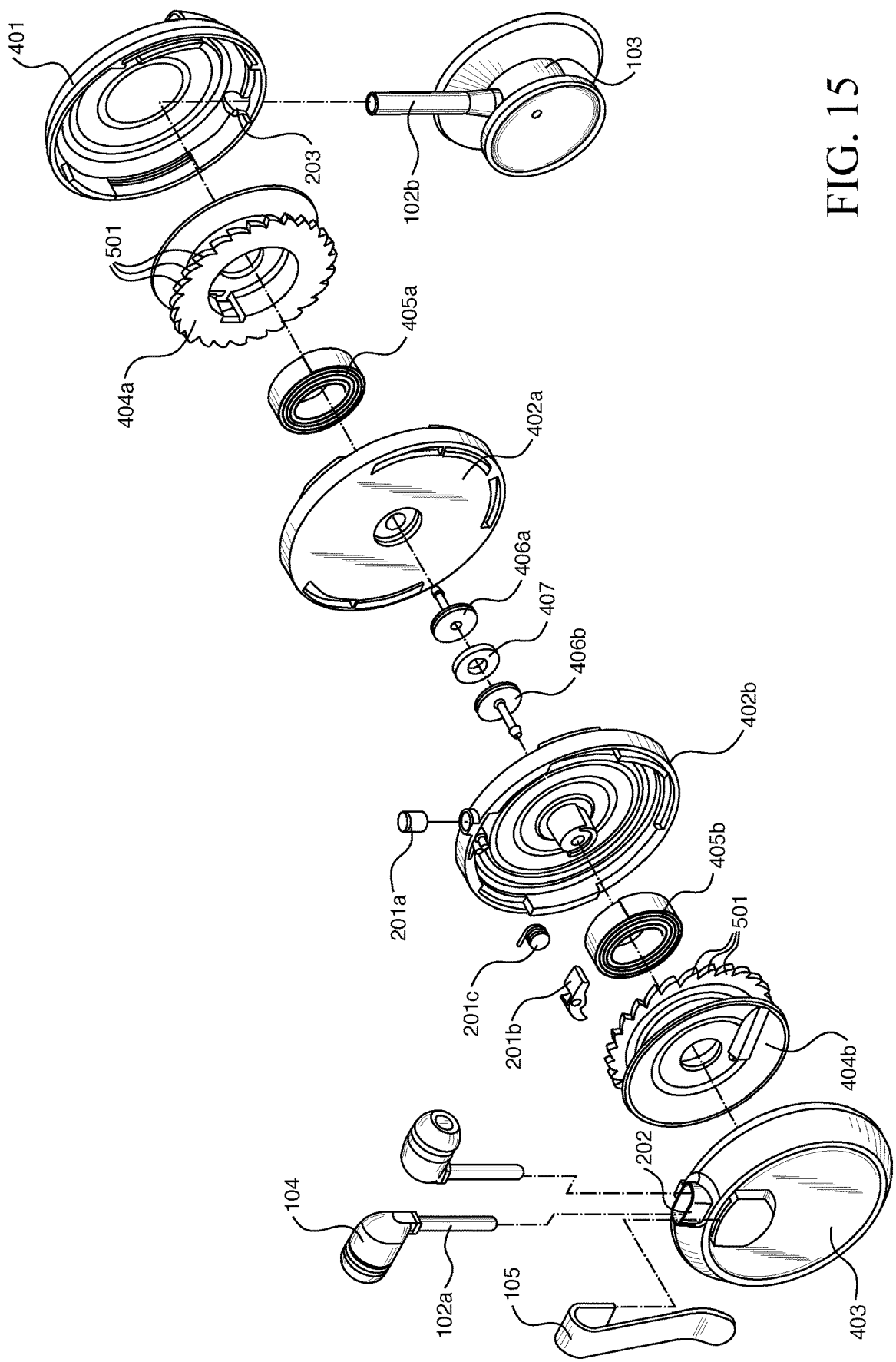
FIG. 15 is an exploded view of a second embodiment of a two-way retractable stethoscope showing the freely rotatable tube connectors that improve mobility of the acoustic tubing.

FIG. 14 shows an exploded view of a two-way retractable stethoscope. A two-way retractable stethoscope may be configured to extend and retract both the ear-piece 104 end and the chest-piece 103 end of the acoustic tubing 102. A two-way retractable stethoscope case 101 may comprise a front case member 401, a center case member 402, and a back case member 403. Within the case 101, the retractable stethoscope may further comprise front and back independently retracting reels 404a, 404b, and front and back reel tension springs 405a, 405b. The acoustic tubing 102 may comprise a top end 102a and a bottom end 102b. The top end 102a may spool around the back independently retracting reel 404b and pass through the top tubing exit 202, and the bottom end 102b may spool around the front independently retracting reel 404a and pass through the bottom tubing exit 203. The top end 102a and the bottom end 102b of the acoustic tubing may be coupled by the center case member 402 such that the chest piece 103 may be in fluid communication with the at least one ear piece 104.

The two-way retractable stethoscope may be configured to lock in various extended positions corresponding to the size and number of locking teeth 501 on one or both of the independently retracting reels 404a, 404b. The retractable stethoscope may also be configured such that one or both of the reel tension springs 405a, 405b may apply a constant rotational force on the corresponding independently retracting reel 404a, 404b. The constant rotational force results in a retracting pull force that is constantly applied to the acoustic tubing 102a, 102b by the corresponding independently retracting reel 404a, 404b. In a constantly retracting configuration, a case 101 may further comprise an extension lock 201 that may comprise a lock top piece 201a coupled by a switch tension spring 201b to a locking switch 201c. The extension lock 201 may relieve and reapply the retracting pull force to the acoustic tubing 102 at the user's will. When engaging or disengaging the extension lock, the user can use the lock top piece 201a which remains accessible when the case is fully assembled.

FIGS. 15 through 18 show views of an exemplary and non-limiting embodiment of a two-way retractable stethoscope. The center case member 402 of this embodiment may further comprise a front and back piece 402a, 402b, front and back tube connectors 406a, 406b, and a gasket 407. Additionally, the acoustic tubing 102 may be configured such that a top end 102a couples to the back tube connector 406b and a bottom end 102b couples with the front tube connector 406a such that the chest piece 103 may be in fluid communication with the at least one earpiece 104. The front and back tube connectors 406a, 406b are freely rotating, increasing the mobility of the acoustic tubing 102 during extension and retraction. The gasket 407 is tightly compressed between the front and back tube connectors 406a, 406b. Alternatively, the tube connectors 406a, 406b and gasket 407 may be exchanged for similar components, such as washers, an axle or spindle, or tacks.

Figure 16:
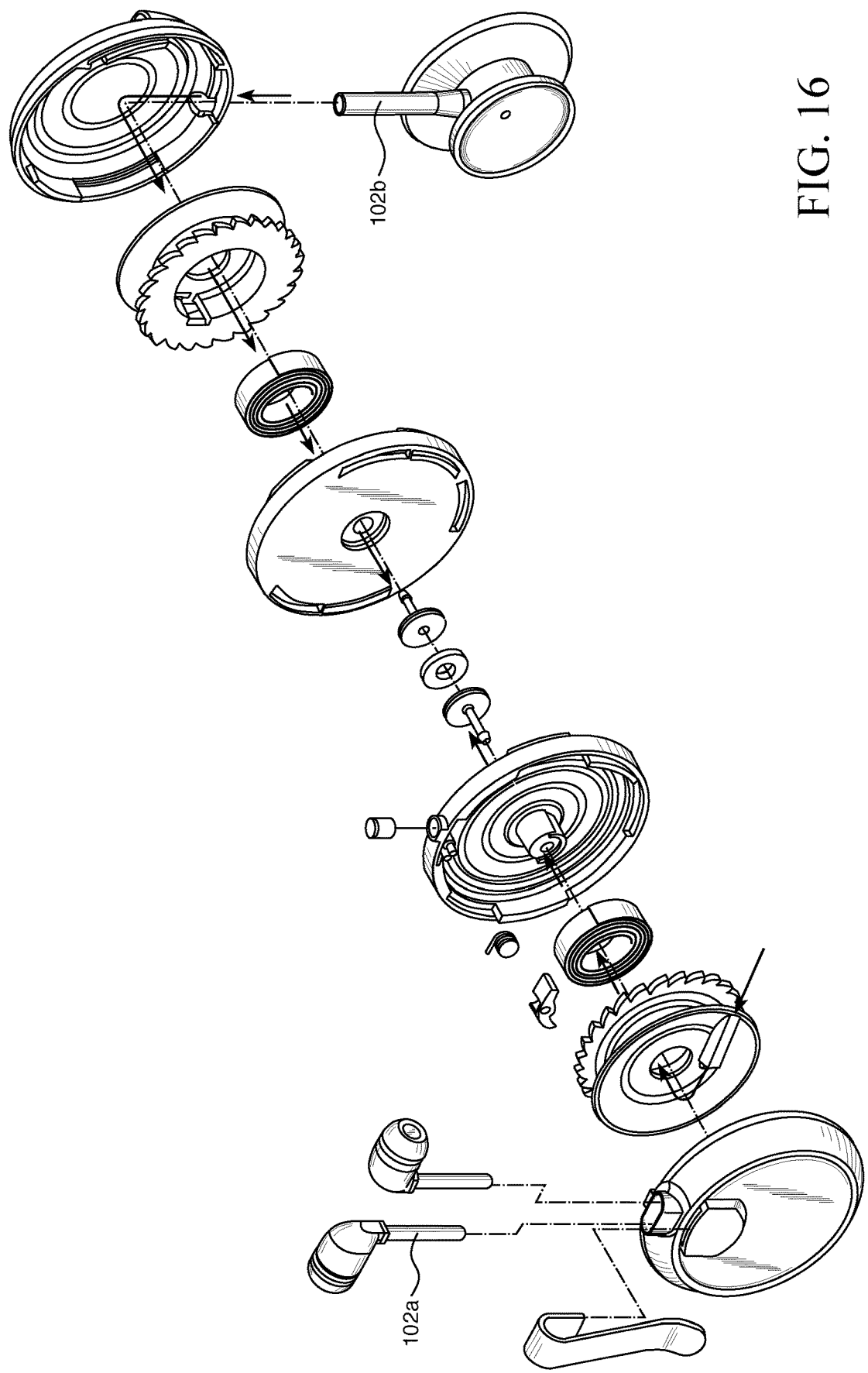
FIG. 16 is an exploded view of a second embodiment of a two-way retractable stethoscope showing the feed-thru path of the acoustic tubing.

As shown in FIG. 16 which provides a non-limiting exemplary embodiment, the acoustic tubing 102 of a retractable stethoscope may be fed through in the following manner: (1) The top end of the acoustic tubing 102a starts where it is coupled to an ear piece 104, then passes through the top tubing exit 202; spools around and feeds through the back independently retracting reel 404b; then passes through the center of the back independently retracting reel 404b, the back reel tension spring 405b, and the back piece of the center case member 402b; and finally couples to the back tube connector 406b. (2) The bottom end of the acoustic tubing 102b starts where it is coupled to the chest piece 103, then passes through the bottom tubing exit 203; spools around and feeds through the front independently retracting reel 404a; then passes through the center of the front independently retracting reel 404a, the front reel tension spring 405b, and the front piece of the center case member 402a; and finally couples to the front tube connector 406a.

Figure 17:
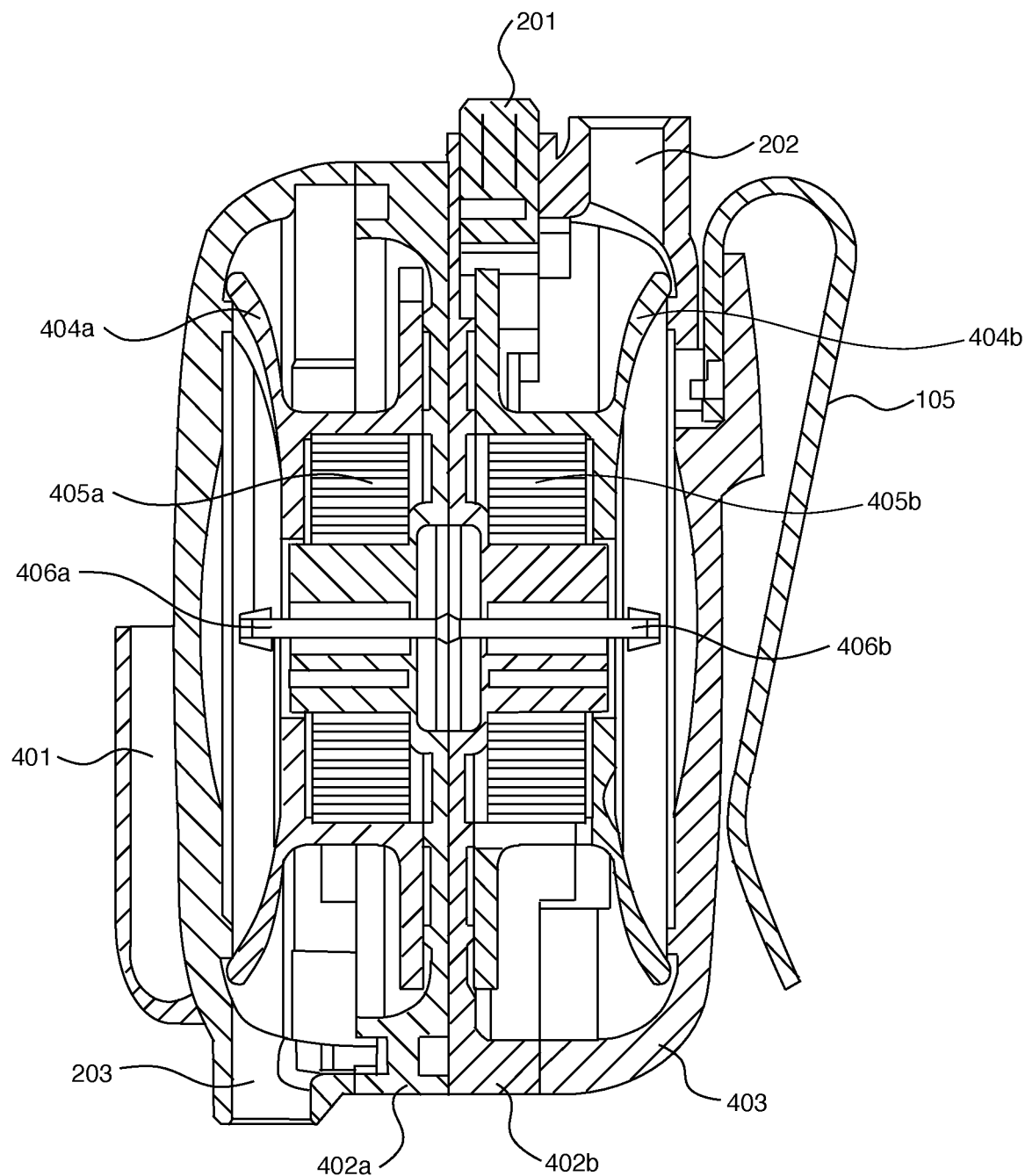
FIG. 17 is a front-to-back cross-sectional view of a second embodiment of a two-way retractable stethoscope showing the reel tension springs and the tube connectors loaded into the reels.
Figure 18:
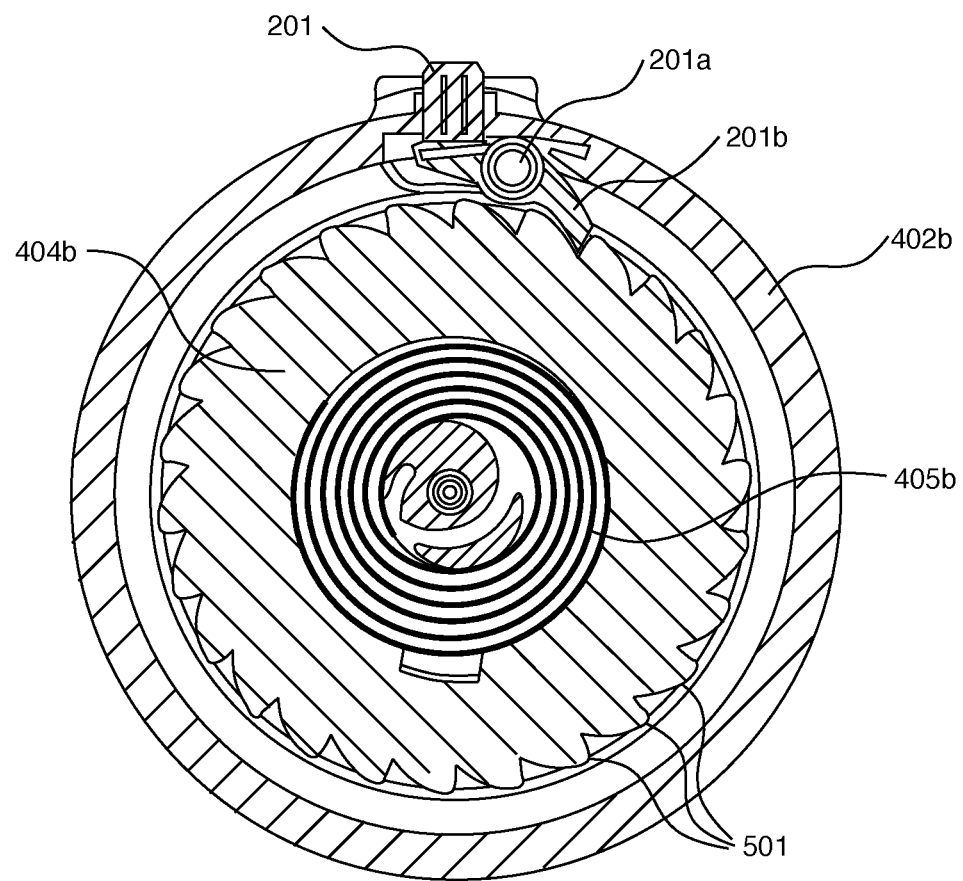
FIG. 18 is a side-to-side cross-sectional view of a second embodiment of a two-way retractable stethoscope showing an extension lock and showing a reel tension spring loaded into a reel.

As shown in FIGS. 17 and 18, the internal components of an embodiment of a retractable stethoscope fit together in a compact manner where the front and back reel tension springs 405a, 405b may be loaded into the front and back independently retracting reels 404a, 404b, respectively. Then, the front and back tube connectors 406a, 406b may be configured head-to-head and pass through the center of the front and back pieces of the center case member 402a, 402b to couple with the bottom and top ends of the acoustic tubing 102b, 102a, respectively. In this configuration, the front and back tube connectors 406a, 406b may be pressed together such that the gasket 407 is tightly compressed between them.

Many of the components of the embodiments described above may be commercially available. Those components that are not commercially available may be manufactured using a variety of materials suitable for their intended purposes, including but not limited to various metals and polymers. Exemplary materials may include 7075 aluminum alloy for the case 101, PVC microbore tubing for the acoustic tubing 102, 102a, 102b, ABS plastic for the reels 303, 404a, 404b and neoprene for the gasket 407. Alternatively, the case 101 may be made of a magnetic material such that a user may quickly access or store the stethoscope on a compatible magnetic surface.

Inventions pertaining to a retractable stethoscope are described above. Various changes may be made to the inventions without departing from their scope. The above descriptions of non-limiting, exemplary embodiments are provided for the purpose of illustration only and not limitation, with the invention being defined by the claims and equivalents thereof.

What is claimed is:

1. A portable retractable acoustic stethoscope, comprising:
    a portable case having a top tubing exit, a bottom tubing exit, and having a retracting reel within the case;
        a first length of acoustic tubing open to atmosphere having one continuous airpath within the acoustic tubing, the first length of the acoustic tubing being housed around the retracting reel, and having one top end extending from the top tubing exit, and
        a second length of acoustic tubing open to atmosphere having one continuous airpath within the acoustic tubing, the second length of acoustic tubing having one bottom end extending from the bottom tubing exit;
    at least one ear piece coupled to the top end of the first length of acoustic tubing; and
    a chest piece coupled to the bottom end of the second length of acoustic tubing;
    wherein each ear piece is in fluid communication with the chest piece via the at least one continuous airpath within the first length acoustic tubing; and
    wherein the first length of the acoustic tubing extends and retracts through the top tubing exit and the second length of acoustic tubing extends and retracts through the bottom tubing exit;
    a front tube connector having a rear end and a first prong portion at a front end, wherein the first prong portion is inserted into a bottom end of the first length of acoustic tubing to maintain fluid communication therebetween;
    a back tube connector having a rear end and a second prong portion at a front end, wherein the second prong portion is inserted into a top end of the second length of acoustic tubing to maintain fluid communication therebetween; and
    a gasket positioned and compressed between abutting rear ends of the front tube connector and the back tube connector such that the chest piece is in fluid communication with the at least one ear piece, wherein, as a function of the gasket, the front tube connector and the back tube connector freely rotate, increasing mobility of the first and second length of acoustic tubing during extension and retraction.

2. The portable retractable acoustic stethoscope of claim 1 further comprising one or both of:
    a switch tension spring coupled to a front reel tension spring or a back reel tension spring to tension the first and second length of acoustic tubing; and
    a locking switch coupled to the front reel tension spring or the back reel tension spring to secure the front reel tension spring or the back reel tension spring with the acoustic tubing.

3. The portable retractable acoustic stethoscope of claim 1 wherein the retractable case further comprises:
    an extension lock configured to lock the first and second length of acoustic tubing in an extended position to prevent retraction through the top tubing exit or the bottom tubing exit.

4. The portable retractable acoustic stethoscope of claim 1 wherein the top tubing exit is oriented in a position approximately 180 degrees from the bottom tubing exit.

5. The portable retractable acoustic stethoscope of claim 4 wherein the first length and the second length of acoustic tubing between the earpiece and the chest piece consists of acoustic tube characterized as having an airpath defined by a continuous circular cross-section throughout the acoustic tube's entire length, and wherein the acoustic tube is configured between a spooled arrangement when retracted and a straight or substantially straight arrangement when extended, such that an acoustic signal traveling through the continuous circular cross-section of the acoustic tube does not encounter a 90 degree turn.

6. The portable retractable acoustic stethoscope of claim 1 wherein the first length and the second length of acoustic tubing between the earpiece and the chest piece consists of a single acoustic tube characterized as having an airpath defined by a continuous circular cross-section throughout the single acoustic tube's entire length, and wherein the single acoustic tube is arranged between a spooled relationship when retracted and a straight or substantially straight relationship when extended, such that an acoustic signal traveling through the continuous circular cross-section of the single acoustic tube does not encounter a 90 degree turn.

7. A portable retractable acoustic stethoscope, comprising:
    a case having a top tubing exit, a bottom tubing exit, a front independently retracting reel,
    a back independently retracting reel, and a center case member, the case including:
        an extension lock configured to lock acoustic tubing in one or more extended positions to prevent retraction through the top tubing exit or the bottom tubing exit;
        a front reel tension spring within the front independently retracting reel;
        a back reel tension spring within the back independently retracting reel;
        a switch tension spring and a locking switch coupled to the front reel tension spring or the back reel tension spring operable, together, to tension and/or secure the acoustic tubing; and
        a lock top piece coupled by the switch tension spring to the locking switch and operable to relieve and/or reapply retracting pull force to the acoustic tubing from one or both tension springs;
        wherein each retracting reel comprises at least one locking tooth configured to lock the acoustic tubing in extended positions corresponding to the size and number of locking teeth;
    a first length of acoustic tubing open to the atmosphere having one top end extending from the top tubing exit, the first length of acoustic tubing having one continuous airpath within the acoustic tubing and being housed around the back the independently retracting reel; and a second length of acoustic tubing open to the atmosphere having one bottom end extending from the bottom tubing exit, the second length of acoustic tubing having one continuous airpath within the acoustic tubing and being housed around the front independently retracting reel;

at least one ear piece coupled to the one top end of the first length of acoustic tubing;

a chest piece coupled to the one bottom end of the second length acoustic tubing;

wherein the one continuous airpath at the one top end of the first length of the acoustic tubing is coupled to the one continuous airpath at the one bottom end of acoustic tubing such that the chest piece is in fluid communication with the at least one ear piece; and wherein the first length of the acoustic tubing extends and retracts through the top tubing exit and the second length of acoustic tubing extends and retracts the bottom tubing exit;

a back tube connector having a rear end and a first prong portion at a front end, wherein the first prong portion is inserted into a bottom end of the first length of acoustic tubing to maintain fluid communication therebetween;

a front tube connector having a rear end and a second prong portion at a front end, wherein the second prong portion is inserted into a top end of the second length of acoustic tubing to maintain fluid communication therebetween; and a gasket positioned and compressed between abutting rear ends of the front tube connector and the second tube connector, wherein, as a function of the gasket, the front tube connector and the back tube connector freely rotate, increasing mobility of the acoustic tubing during extension and retraction.

8. The portable retractable acoustic stethoscope of claim 7 wherein the retractable stethoscope further comprises: a belt clip coupled to the case.

9. The portable retractable acoustic stethoscope of claim 7 wherein the top tubing exit is oriented in a position approximately 180 degrees from the bottom tubing exit.

10. The portable retractable acoustic stethoscope of claim 9 wherein the first length and the second length of acoustic tubing between the earpiece and the chest piece consists of acoustic tube characterized as having an airpath defined by a continuous circular cross-section throughout the acoustic tube's entire length, and wherein the acoustic tube is configured between a spooled arrangement when retracted and a straight or substantially straight arrangement when extended, such that an acoustic signal traveling through the continuous circular cross-section of the acoustic tube does not encounter a 90 degree turn.

11. The portable retractable acoustic stethoscope of claim 7 wherein the first length and the second length of acoustic tubing between the earpiece and the chest piece consists of acoustic tube characterized as having an airpath defined by a continuous circular cross-section throughout the acoustic tube's entire length, and wherein the acoustic tube is configured between a spooled arrangement when retracted and a straight or substantially straight arrangement when extended, such that an acoustic signal traveling through the continuous circular cross-section of the acoustic tube does not encounter a 90 degree turn.

12. A portable retractable acoustic stethoscope, comprising:

a case having a top tubing exit, a bottom tubing exit, a front independently retracting reel, a back independently retracting reel, a front tube connector, a back tube connector, and a gasket, wherein the gasket couples together the front tube connector and the back tube connector;

a first length of acoustic tubing open to the atmosphere having one top end extending from the top tubing exit, the first length of acoustic tubing having one continuous airpath within the acoustic tubing and being housed around the back independently retracting reel, wherein the first length of acoustic tubing couples to the back tube connector, and a second length of acoustic tubing open to the atmosphere having one bottom end extending from the bottom tubing exit, the second length of acoustic tubing having one continuous airpath within the acoustic tubing and being housed around the front independently retracting reel, wherein the second length of acoustic tubing couples to the front tube connector;

at least one ear piece coupled to the one top end of the first length of acoustic tubing;

a chest piece coupled to the one bottom end of the second length of acoustic tubing;

wherein one continuous airpath at the one top end of the first length of acoustic tubing is coupled to the one continuous airpath at the one bottom end of the second length of acoustic tubing such that the chest piece is in fluid communication with the at least one-ear piece; and wherein the first length of the acoustic tubing extends and retracts through the top tubing exit and the second length of acoustic tubing extends and retracts through the bottom tubing exit;

the back tube connector having a rear end and a first prong portion at a front end, wherein the first prong portion is inserted into a bottom end of the first length of acoustic tubing to maintain fluid communication therebetween;

the front tube connector having a rear end and a second prong portion at a front end, wherein the second prong portion is inserted into a top end of the second length of acoustic tubing to maintain fluid communication therebetween; and wherein the gasket is positioned and compressed between abutting rear ends of the front tube connector and the second tube connector such that the chest piece is in fluid communication with the at least one ear piece via a single continuous acoustic airpath throughout the first length of acoustic tubing and the second length of acoustic tubing, wherein, as a function of the gasket, the front tube connector and the back tube connector freely rotate and thereby increase mobility of the acoustic tubing during extension and retraction.

13. The portable retractable acoustic stethoscope of claim 12 wherein the case further comprises:

an extension lock configured to lock one or both of the first length and/or the second length of acoustic tubing in an extended position to prevent retraction through the top tubing exit or the bottom tubing exit.

14. The portable retractable acoustic stethoscope of claim 12 wherein at least one of the front and back independently retracting reels within the case further comprise:

a plurality of locking teeth configured to lock one or both of the first length and/or the second length of acoustic tubing in extended positions corresponding to the size and number of the locking teeth.

15. The portable retractable acoustic stethoscope of claim 12 wherein the retractable stethoscope further comprises: a belt clip coupled to the case.

16. The portable retractable acoustic stethoscope of claim 12 wherein the top tubing exit is oriented in a position approximately 180 degrees from the bottom tubing exit.

17. The portable retractable acoustic stethoscope of claim 12 wherein the first length and the second length of acoustic tubing between the earpiece and the chest piece consists of acoustic tube characterized as having an airpath defined by a continuous circular cross-section throughout the acoustic tube's entire length, and wherein the acoustic tube is configured between a spooled arrangement when retracted and a straight or substantially straight arrangement when extended, such that an acoustic signal traveling through the continuous circular cross-section of the acoustic tube does not encounter a 90 degree turn.

\* \* \* \* \*